US007625550B2

(12) United States Patent
Yang et al.

(10) Patent No.: US 7,625,550 B2
(45) Date of Patent: Dec. 1, 2009

(54) ENHANCED RESOLUTION OF TUMOR METASTASIS USING A SKIN FLAP MODEL

(75) Inventors: Meng Yang, San Diego, CA (US); Eugene Baranov, San Diego, CA (US); Jin Wei Wang, San Diego, CA (US)

(73) Assignee: Anticancer, Inc., San Diego, CA (US)

( * ) Notice: Subject to any disclaimer, the term of this patent is extended or adjusted under 35 U.S.C. 154(b) by 52 days.

(21) Appl. No.: 10/241,362

(22) Filed: Sep. 10, 2002

(65) Prior Publication Data

US 2003/0088885 A1    May 8, 2003

Related U.S. Application Data

(60) Provisional application No. 60/322,291, filed on Sep. 10, 2001.

(51) Int. Cl.
*A61B 5/00* (2006.01)
*A61B 10/00* (2006.01)
*A61K 49/00* (2006.01)
*C12N 15/00* (2006.01)

(52) U.S. Cl. .................. 424/9.6; 424/9.1; 435/440; 435/455

(58) Field of Classification Search .............. 424/9.6, 424/9.1; 435/440, 455
See application file for complete search history.

(56) References Cited

U.S. PATENT DOCUMENTS

| | | | | |
|---|---|---|---|---|
| 6,232,523 | B1 | 5/2001 | Tan et al. | 800/10 |
| 6,235,967 | B1 | 5/2001 | Tan et al. | 800/10 |
| 6,235,968 | B1 * | 5/2001 | Tan et al. | 800/10 |
| 6,251,384 | B1 | 6/2001 | Tan et al. | 424/93.21 |

FOREIGN PATENT DOCUMENTS

| | | |
|---|---|---|
| WO | WO 98/49336 | 11/1998 |
| WO | WO 00/40274 | 7/2000 |

OTHER PUBLICATIONS

Verkhusha et al. (2001) An enhanced mutant of Red Flourescent Protein DsRed for double labeling and Devlopmental timer of Neural Fiber Bundle Formation. J. Biol. Chem. 276: 29621-29624.*
Zhang et al. (1996) An Enhanced Green Flurescent Protein allows Sensitive Detection of Gene Transfer in Mammalian Cells. Biochem. Biophys. Res. Comm. 227:707-711.*
McCart et al. (2001) Systemic Cancer Therapy with Tumor-selective Vaccinia Virus Mutant Lacking Thymidine Kinase and Vaccinia Growth Factor Genes. Cancer Research 61:8751-8757.*
Dunn et al (2000) Influence of Optical Poperties on Two-photon Flourescence imgaing in turbid samples. Applied Optics 39:1194-1201.*
Runkel et al. (1991) An Intradermal Assay for Quantification and Kinetics Studies of Tumor Angiogenesis in Mice. Radiation Research 126:237-243.*
Naumov et al. (1999) Cellular expression of Green fluorescent protein, coupled with high-resolution in vivo videomicroscopy, to monitor steps in tumor metastasis. J. of Cell Science 112:1835-1842.*
The American Heritage® Dictionary of the English Language at (http://www.thefreedictionary.com/body+wall) pp. 1 and 2.*
The American Heritage® Dictionary of the English Language, Fourth Edition, 2003, at http://www.thefreedictionary.com/body+wall, pp. 1-2.*
Condeelis, J.S. et al., "Imaging of Cancer Invasion and Metastasis Using Green Fluorescent Protein" European Journal of Cancer 36:1671-1680 (2000).
Hoffman, R.M. et al., "Visualization of GEP-Expressing Tumors and Metastasis In Vivo" BioTechniques 30:1016-1026 (2001).
Brown et al. "In Vivo Measurement of Gene Expression, Angiogenesis and Physiological Function in Tumors Using Multiphoton Laser Scanning Microscopy" Nat. Med. (2001) 7:864-868.
Ciancio et al. "Cutaneous Window for In Vivo Observations of Organs and Angiogenesis" J. Surg. Res. (2000) 92:228-232.
Naumov et al. "Cellular Expression of Green Fluorescent Protein, Coupled with High-Resolution In Vivo Videomicroscopy, to Monitor Steps in Tumor Metastasis" J. Cell Sci. (1999) 112:1835-1842.
Yang et al. "Direct External Imaging of Nascent Cancer, Tumor Progression, Angiogenesis, and Metastasis on Internal Organs in the Fluorescent Orthotopic Model" Proc. Natl. Acad. Sci. (2002) 99:3824-3829.
Farina et al., Cancer Research (1998) 58(12):2528-2532.
Gelaw et al., Surgery (2001) 130(3):497-501.
Li et al., Journal of the National Cancer Institute (2000) 92(2):143-147.
Rashidi et al., Clinical and Experimental Metastasis (2000) 18:57-60.
Yang et al., PNAS USA (2001) 98(5):2616-2621.
Yang et al., PNAS USA (2000) 97(3):1206-1211.
Yang et al., PNAS USA (2000) 97(22):12278-12282.
Yang et al., Clinical and Experimental Metastasis (1999) 17(5):417-422.
Yang et al., Cancer Research (1999) 59(4):781-786.
Notice of Reasons for Rejection for Japanese Patent Application No. 2003-526186, mailed on May 7, 2008, 2 pages.
Zhou et al., Cancer Gene Therapy (2002) 9:681-686.
Falk et al., Microscopy Research and Technique (2001) 52:251-262.
Notice of Reasons for Rejection for Japanese Patent Application Serial No. 2003-526186, mailed on Mar. 31, 2009, 2 pages.
Werdien et al., Nucleic Acids Research (2001) 29(11):e53.

* cited by examiner

*Primary Examiner*—Anne-Marie Falk
(74) *Attorney, Agent, or Firm*—Morrison & Foerster LLP (57) ABSTRACT

A enhanced method for observing tumor progression, angiogenesis and/or metastasis in animal models in real time is described. The invention employs a skin flap over the area to be observed that can be opened and closed reversibly. The invention also permits simultaneous observation of more than one tumor by use of multiple colors.

17 Claims, 8 Drawing Sheets

ENHANCED RESOLUTION OF TUMOR METASTASIS USING A SKIN FLAP MODEL

This application claims priority under 35 U.S.C. §119(e) to U.S. provisional application Ser. No. 60/322,291 filed 10 Sep. 2001. The contents of which are incorporated herein by reference.

TECHNICAL FIELD

The invention is directed to an improved method to follow tumor growth and metastasis by enhancing resolution so that even single cells can be detected in vivo. This is accomplished by use of a skin flap which is tolerated by the living animal. A method for multicolor labeling is also disclosed.

BACKGROUND ART

U.S. Pat. Nos. 6,232,523; 6,235,967; 6,235,968; and 6,251,384, as well as PCT applications PCT US 98/08457 and PCT US 00/00243, all of which are incorporated herein by reference, describe techniques for labeling tumors and their metastases using fluorescent markers, especially green fluorescent protein (in various colors) as well as detecting angiogenesis using this type of labeling, optionally along with a contrast dye. According to the descriptions of these documents, it is possible to detect tumor progression, angiogenesis, and metastasis by excising the tumor tissue, or, perhaps more benevolently, in real time by following the course of the condition through whole body imaging. The imaging of this condition through the skin has been successful, but, not surprisingly, is somewhat limited in sensitivity due to scattering through the skin. Others have attempted to overcome the lack of sensitivity by invasive techniques which are of only modest success. For example, Brown, E B, et al., *Nat Med*, (2001) 7:864-868 used a dorsal skin chamber in mice with two photon confocal microscopy. Such an approach is limited to ectopic primary tumors. Naumov, G N, et al., *J Cell Sci* (1999) 112:1835-1842 described intravital microscopy of GFP-expressing tumors on exteriorized organs. This had the effect of serious morbidity. Subcutaneous windows of semitransparent materials are described by Siancio, S J, et al., *J Surg Res* (2000) 92:228-232. All of these methods suffer from serious disadvantages, not the least of which is that they are not suitable for repetitive measurement and cause serious harm to the model, thus distorting the results, as well as being capable only of limited time duration.

It is has now been found that by providing a simple skin flap, which can be opened and then resutured, an enhanced sensitivity, permitting observation of as little as a single cell, can be obtained while maintaining the subject in observable condition. The technique is minimally invasive and thus permits observation of tumor progression, angiogenesis, and metastasis with great precision often to a single cell level. Since the skin flap technique is relatively harmless, observation at later stages in the development of the tumor and its metastasis is possible. The intact animal is maintained. The ability to observe over long time periods also permits detection of dormant walls.

A report of this work was published by the present applicants in March of 2002: Yang, M., et al., *Proc Natl Acad Sci* (2002) 99:3824-3829. The contents of this publication are incorporated herein by reference.

DISCLOSURE OF THE INVENTION

The invention is directed to improvements in model systems for observing the progression of tumors as well as angiogenesis and metastasis thereof. The method employs fluorescent labeling of the tumor, which can be implanted in ways generally known in the art, and observing by fluorescent emission. In an improved method of the invention, a skin flap is provided which can be reversibly opened and closed; when the observations are made through the opened skin flap, a high sensitivity and precision of observation are obtained. In another aspect, more than one tumor may be observed simultaneously.

Thus, in one aspect, the invention is directed to a method to monitor tumor progression, angiogenesis and/or metastasis on the internal organs of a tumor model system, which system is an immunocompromised or syngeneic experimental animal, which method comprises observing fluorescent tumor cells in said model system through an opened skin flap; wherein said skin flap is reversibly opened and closed.

In another aspect, the invention is directed to a method to evaluate the effect of compounds or protocols on cancer progression, angiogenesis and/or metastasis which method comprises carrying out the foregoing method in the presence and absence of the compound or protocol to be tested and comparing the results obtained. A reduction in tumor progression, angiogenesis and/or metastasis in the presence as opposed to the absence of the compound or protocol indicates that compound or protocol is a successful candidate for anti-tumor therapy.

In the foregoing methods, the tumor cells may be labeled with fluorescent dyes as generally known in the art. Preferably, auto-fluorescent proteins (generally known as green fluorescent protein GFP) may be used. It is well known that "GFP" is a generic name for various colors of fluorescent protein. Sometimes alternative designations for different colors are used. However, as used herein, "GFP" refers to a fluorescent protein of whatever wavelength emitted. When specifically a different color is intended, this may be designated as well, e.g., red fluorescent protein (RFP).

According to one embodiment of the method of the invention, tumors may be labeled with different colors and followed simultaneously.

The methods of the invention have a number of advantages. First, enhanced sensitivity permits observation of only a single or two cells. Second, angiogenesis is directly observable, which is extremely important in evaluating therapeutic efficacy of proposed compounds and protocols. Third, it is possible to observe two tumors simultaneously. This is especially important because of the phenomenon of interference between disparate tumors. Since two different colors can be used, the interaction of two separate tumors can be observed directly. Fourth, because it is possible to make observations over substantial periods of time, distinctions can be made between tumor cells that are actively proliferating and dormant cells. Thus, the presence of dormant cells can be determined by the method of the invention.

BRIEF DESCRIPTIONS OF THE DRAWINGS

Of FIGS. 3A-3C show macro imaging and microscopic imaging of BxPC-3-GFP human pancreatic tumor angiogenesis through the abdominal wall skin flap window.

MODES OF CARRYING OUT THE INVENTION

The invention is focused on providing a reversible means for making sensitive observations of fluorescently labeled cells in animal tumor models. The animal models are most typically rodents which are immunocompromised, such as SCID mice, nude mice, immunocompromised rats, as well as guinea pigs, rabbits and the like. Theoretically, there is no reason that the studies cannot be conducted on other immunocompromised animals, including avian subjects. However, because rats and mice are convenient laboratory tools, it is most frequently encountered that the invention involves use of these established tumor models. Alternatively, the animals may be syngeneic to the tumors; there are many such models available.

The material used to label the tumor cells is a proteinaceous material which emits observable light. The tumor cells are typically modified to contain an expression system for a fluorescent protein, as the fluorescent moiety will be provided to the daughter cells as the tumor proliferates. While it is possible to use proteins that fluoresce as a result of metabolic events, such as luciferase, it is preferred to use fluorescent proteins that have this property by virtue of there being provided an excitation wavelength. Preferred among these fluorescent labels are the various colors of green fluorescent protein, a labeling system by now well established in the art. As is understood, the specific form of fluorescent protein can be modified if necessary to be immunocompatible with the host organism or to enhance expression in such organisms. However, as the fluorescent protein is provided intracelluarly within the tumor cells, immunogenicity is generally not problematic with respect to the protein itself. The protein is effectively insulated form the immune system of the model.

The tumor cells may be provided with an expression system for one or more fluorescent proteins using standard methods. The cells may be transduced in vitro and grown into tumors in vitro or in vivo and the resulting tumors transplanted in to the model subject. The cells may be injected or may be transplanted surgically. Surgical orthotopic transplantation is particularly preferred; however, other methods of providing the model with modified tumor cells which stably express the fluorescent protein may also be used. In addition, the model which bears an endogenous tumor or introduced tumor may be provided with a viral vector, particularly a retroviral vector, for expression of the protein which infects the tumor already present in the animal. This vector is preferably introduced locally to the already present tumor.

Any model of tumor progression, angiogenesis, and/or metastasis which relies for observation on the emission of fluorescence may be used in the method of the invention. The invention method involves providing a skin flap which can be reversibly opened and closed. Typically, after anesthetizing the animal, an arc-shaped incision is made in the skin and subcutaneous connective tissue is separated to free the skin flap. The flap can be closed by suturing.

The ability to observe, directly through the opened skin flap, the labeled tumor cells greatly enhances the sensitivity and resolution of the model system of the invention. The model can be used simply to monitor the progress of the condition or can be used as a means to evaluate potential therapeutics, as well as to evaluate effects which may result in more negative outcomes than no treatment at all. In this instance, a compound and/or protocol is supplied to test animals and compared to controls where the compound and/or protocol are not present. Enhancement of tumor progression, angiogenesis and/or metastasis in the presence of these experimental conditions indicates that the compound and/or protocol is deleterious to the subject; similarly, inhibition of any of these features identifies the compound and/or protocol as a potential therapeutic.

In many instances, a single color is used to observe the metastasis of a single tumor. However, the method of the invention includes simultaneous observation of two or more tumors each labeled with a different color of fluorescent protein. By utilizing this method, not only is it possible to obtain multiple observations of multiple tumor progressions, the effects or interferences of each tumor on the other can be observed directly.

The following examples are intended to illustrate but not to limit the invention.

Preparation A—Preparation of Green Fluorescent Tumor Cell Lines

Human and animal tumor cells, which are 20-40% confluent were incubated with 1:1 precipitated mixture of retroviral supernatants of PT67 packaging cells in RPMI medium 1640 or other media containing 10 percent (v/v) FBS for 72 hours. The supernatants were from PT67 cells cultured in DMEM supplemented with 10 percent v/v heat inactivated FBS. The packaging cells at 70 percent confluence were incubated with a precipitated mixture of DOTAP transfection reagent and saturating amounts of pLEIN for 18 hours. Medium was replenished at this time and cells were examined by fluorescent microcopy 48 hours after transfection. The cells were cultured in the presence of 500-2,000 mg/ml of G418 increased in step-wise manner for selection. The pLEIN vector, obtainable from CLONTECH, expresses enhanced green fluorescent protein and the neomycin resistance gene on the same bicistronic message that contains an internal ribosome expression site. Human U87 glioma tumor cells, mouse Lewis lung carcinoma cells, human BxPC-3-carcinoma cells and rat Dunning prostate carcinoma cells were prepared in this way.

Fresh medium was replenished and the tumor cells were reharvested with trypsin/EDTA and subcultured at 1:15 into selected medium that contained 50 μg/ml of G418. This level was increased step-wise to 800 μg/ml. Clones expressing GFP were isolated with cloning cylinders (Bell-Art Products) by trypsin/EDTA and were amplified and transferred conventionally in the absence of selective agent.

Preparation B—Cancer Cell Lines Expressing RFP

Dunning prostate cancer cells were cultured in RPMI medium 1640 containing 10% v/v FBS and then incubated with a precipitated mixture of Lipofetamine Plus (GIBCO) and saturating amounts of RFP-expressing pLNCX$_2$ DS Red 2 plasmid for 6 hours before replenishing with fresh medium. The expression vector was obtained by inserting DS Red 2 into the pLNCX$_2$ vector at the Egl II and NotI sites. Both of these materials are obtainable from CLONTECH.

The cells were harvested with trypsin/EDTA 48 hours after transfection and subcultured at 1:15 into selective medium containing 200 μg/ml G418 cells with stably integrated plasmids were selected by growing transiently transfected cells in 200 μg/ml G418 and isolated with cloning cylinders as above.

Preparation C—Preparation of Tumor Tissue

To obtain tumor tissue stock, six-week-old Nu/Nu female mice were injected SC with a single dose with $10^6$-$10^7$ GFP or RFP expressing tumor cells. The cells were harvested by trypsinization, washed three times with cold serum-containing medium and kept on ice; then injected in the S.C. space on the flank at a total volume of 0.2-0.4 ml within 40 minutes of harvesting. Tumor tissue was harvested 3-6 weeks after injection for surgical orthotopic implantation of tumor fragments.

EXAMPLE 1

Brain Cancer Model

The parietal bone of the skull was exposed after an arc-shaped scalp incision. Twenty ml containing 5×$10^5$ U87-GFP cells are per mouse were injected into the right parietal lobe with a 1 ml 27G ½ latex-free syringe. The incision was closed with a 7-0 surgical suture in one layer. The animals were kept under is isoflurene anesthesia during surgery. For observation, the skin flap was opened and observed with a Leica fluorescent stereo microscope model L212 equipped with a mercury 50 watt lamp power supply. Fluorescence was observed through a 520 nanometer long pass filter. Images from the microscope and light box were captured on a Hamamatsu 3518103 chip Cool Color charge-coupled device camera.

Images were processed for contrast and brightness and analyzed with the use of image Pro Plus V40 software. High-resolution images of 1024×724 pixels were captured directly on an IBM PC or continuously through video output on a high-resolution Sony VCR model SLVR1000. These procedures and equipment are described by Yang, M, et al., *Proc Natl Acad Sci USA* (2000) 97:1206-1211; Yang, M, et al., *Ibid.* (2001) 98:2616-2621; Yang, M, et al., *Ibid.* (2000) 97:12278-12282, all incorporated herein by reference.

Figure 1:
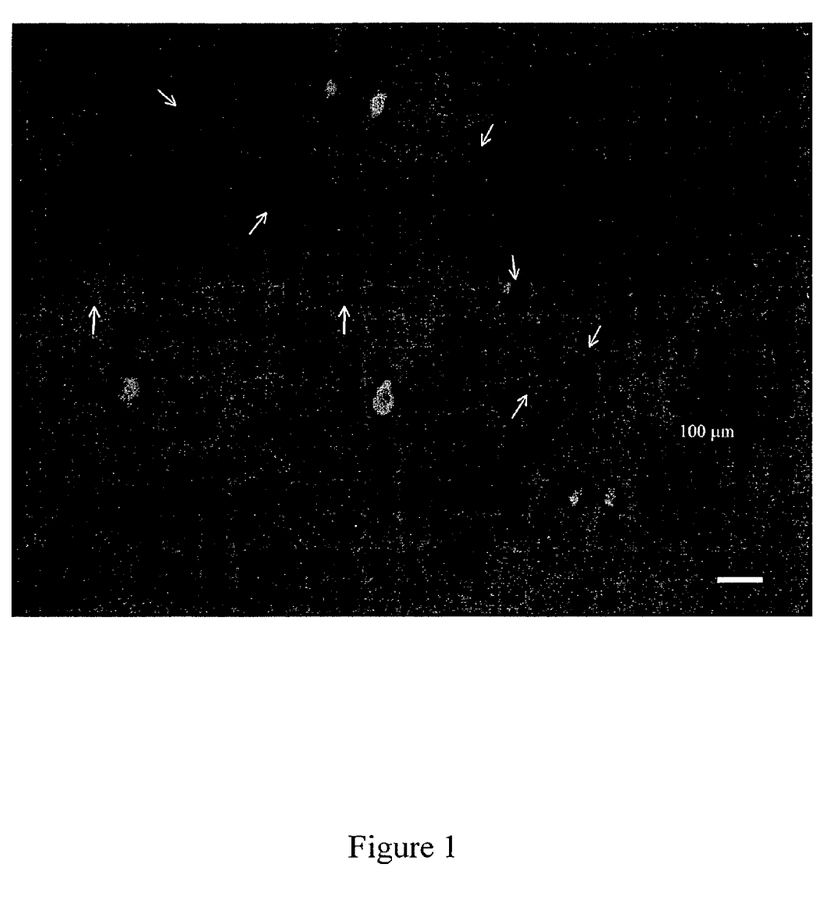
FIG. 1 shows a image through the scalp-flap window of single tumor cells that separated from a bolus of U87-GFP tumor cells. The bar is 100 μm.

A quantitative measurement of the fluorescence with the skin flap opened shows a 20-fold increase in intensity when intervening scalp tissue is removed. An area was observed wherein single fluorescent cells are clearly resolved and which could not be imaged to the scalp. See FIG. 1.

EXAMPLE 2

Lung Cancer Model

Tumor pieces 1 mm$^3$ from the tumor formed from GFP Lewis lung carcinoma were implanted by SOI into the left visceral pleura of nude mice. The mice were anesthetized by isofluorene and a small 1 centimeter transverse incision was made on the left lateral chest through the fourth intercostal space. A small incision provided access to the pleural space and resulted in total lung collapse. Two tumor pieces were sown together with an 8-0 nylon surgical suture and fixed by making one knot. The lung was taken up by forceps and the tumor pieces sown into the lower part of the lung with one suture. The lung tissue was returned in to the chest cavity and the chest muscles and skin closed with a single layer of 6-0 silk sutures. The lung was reinflated by withdrawing air from the chest cavity with a 23 gauge needle. These procedures were performed with a 7× dissection microscope.

Using the observation techniques described in Example 1, the whole body image through the skin was compared with external direct view images when the skin flap was opened. The direct view image showed tumor microfoci and angiogenic vessels on the primary tumor which were not seen through the skin. Images of primary tumor and microfoci progression were recorded over a six-day period and tumor growth curves were constructed. The congruence between data points and expected growth curve shows the technique yields active quantitative measurements. Microfoci as small as one or two cells on the ipsilateral lung could be imaged with the skin flap opened on day 5. Microfoci seeded by metastasis could also be observed on the contralateral lung on day 7.

EXAMPLE 3

Liver Metastasis Models

Tumor fragments from AC34862 tumors stably expressing GFP were implanted by SOI on the colon in nude mice. A lower mid-line abdominal incision permitted exposure of the colon and the serosa was removed and two pieces of 1 mm$^3$ tumor fragments were implanted. A 8-0 surgical suture was used to penetrate the small tumor pieces and suture them to the wall of the colon which was then returned to the abdominal cavity. The incision in the abdominal wall was closed with a 7-0 surgical suture. The animals were anesthetized with a ketamine mixture of Ketoset and PromAce and xylazine hydrochloride. The procedures were performed with the 7× dissection microscope.

When observation was made as described in Example 1, metastatic microfoci were visible by day 7 after implantation. Two metastatic lesions of 150 μm and 300 μm were externally imaged through the opened skin flap over the abdominal wall. The 150 μm lesion was formed from a single-tumored microfocus; the 300 μm lesion had 5 separate colonies, the largest of which was located in the center of the lesion. Four smaller microfoci ranging from 80-100 μm were also observed.

In an alternative model, 100 μm containing $10^6$ Colo 320 GFP cells were injected in the portal vein with a 1 ml 39 GI laytex-free syringe; the portal vein was exposed after an upper midline abdominal incision. The puncture hole in the vein was pressed for about 10 seconds with a sterile cotton bar and the incision closed with a 7-0 surgical suture in one layer. A ketamine mixture anesthesia and the 7× dissection microscope were used. Using the observation methods of Example 1, microfoci and single cells were visible in the liver when externally viewed through an opened skin flap.

Figure 2:
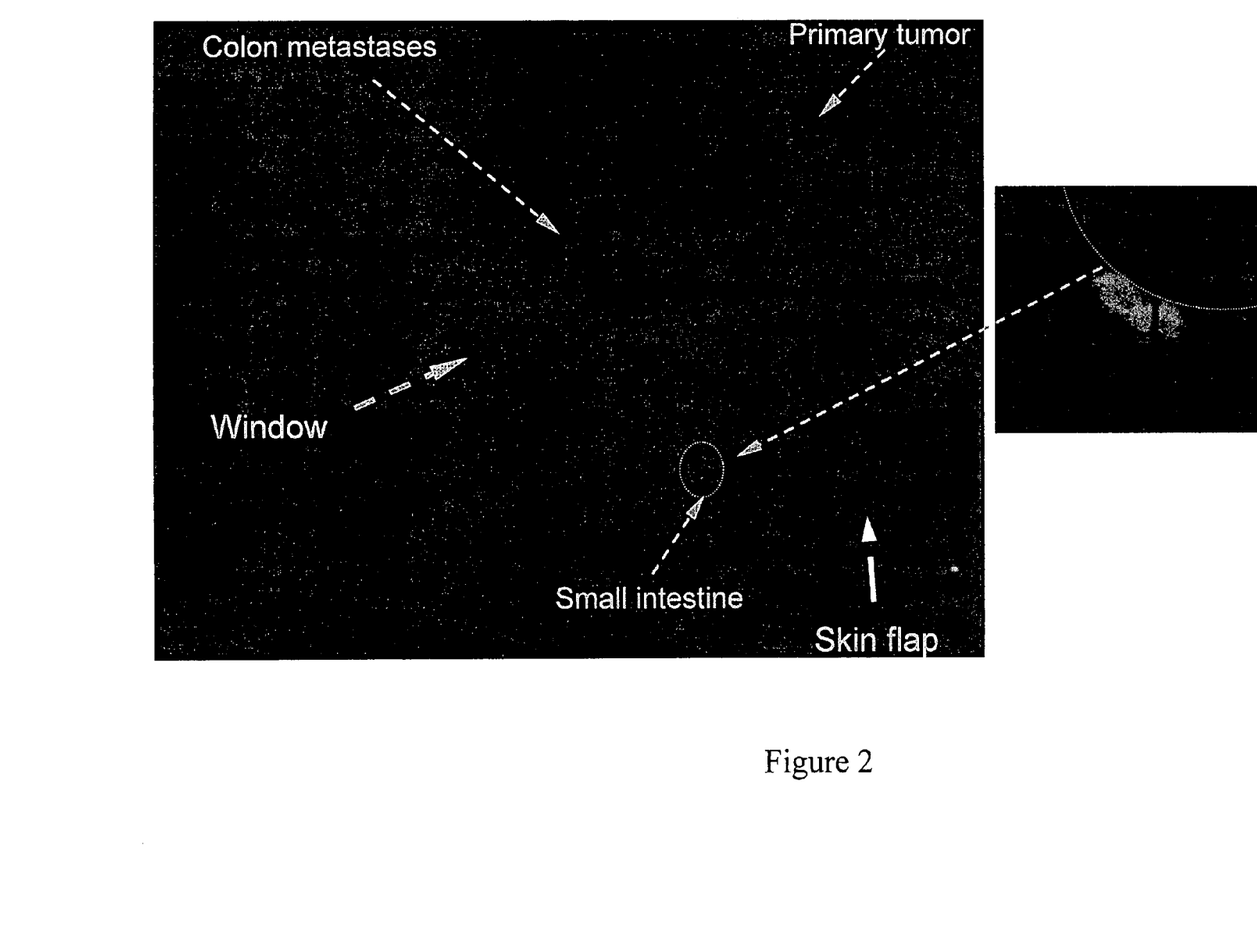
FIG. 2 shows imaging through an abdominal wall skin flap window of Colo 205 human cancer metastasis in the small intestine.

In a similar experiment, Colo 205 GFP cells were used, and FIG. 2 shows imaging, through the open skin flap including a 40× magnification.

EXAMPLE 4

Pancreatic Cancer Model

Figure 3A:
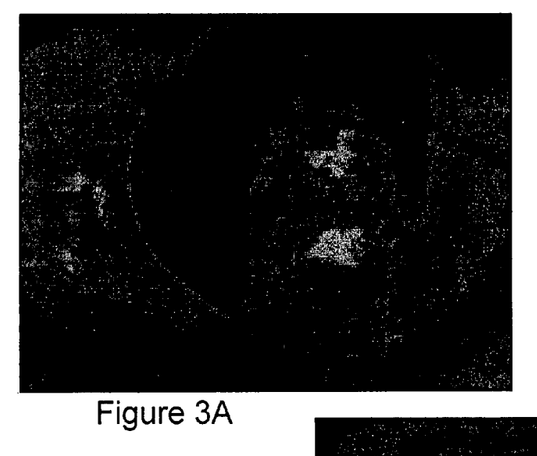
Figure 3B:
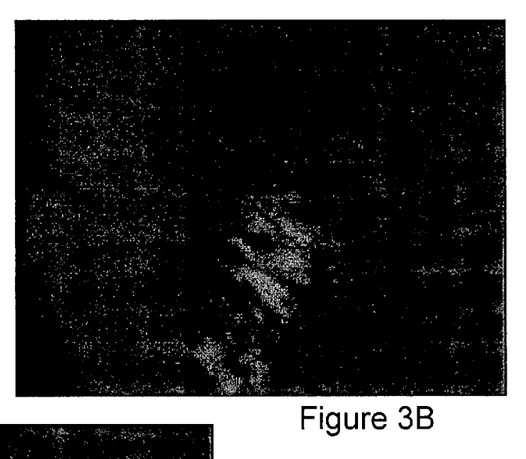
Figure 3C:
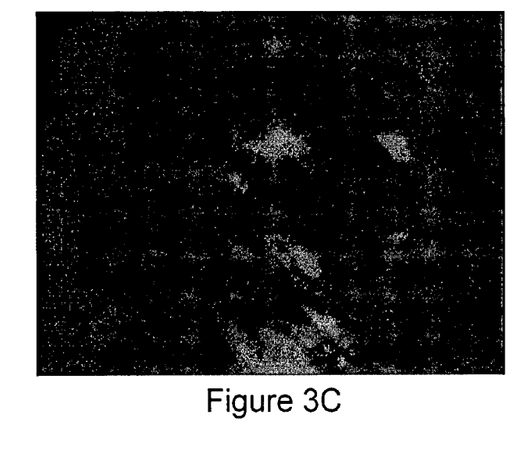

Nude mice were anesthetized using a ketamine mixture and the abdomens sterilized with alcohol. An incision was made through the left-upper abdominal para rectal line and peritoneum to expose the pancreas. Three tumor pieces 1 mm$^3$ of BxPC3 human pancreatic tumor expressing GFP, which had been excised from the nude mice described in Preparation C and kept in Hanks balanced salt solution (containing 100 units per ml penicillin and 100 units per ml of streptomycin) were transplanted on the middle of the pancreas with a 6-0 Dexon surgical suture. The pancreas was returned to the cavity and the abdominal wall and the skin closed with a 6-0 Dexon suture. Again, the 7 dissection microscope was used. Imaging of the tumor through the opened skin flap according to Example 1 showed the tumor surrounded by its microvessels which are visible as dark shadows. Observation of these vessels are not possible with the skin flap closed. FIGS. 3A-3C show the clear visibility of angiogenesis. FIG. 3A shows macroimaging through the skin flap window; FIGS. 3A and 3B show images through the skin flap at 20× and 40× magnification respectively.

EXAMPLE 5

Prostate Cancer Model

Dunning prostate carcinoma expressing either GFP or RFP were obtainined from nude mice as described in Preparation C. One mm$^3$ sections of the tumor were composed of viable cells and were kept under sterile conditions. Mice were anesthetized with a ketamine mixture and positioned supinely. An arc-shaped skin flap was made right above the pubis symphysis to expose the prostate gland. The fascia surrounding the ventral portion of the prostate was isolated and two ventral lateral lobes of the gland were exposed by a small incision. One piece of Dunning-GFP tissue was sutured into one lobe with an 8-0 nylon suture and one piece of Dunning-RFP was sutured into the other lobe. The abdomen was closed with a 6-0 suture. As above, the 7× dissection microscope was used.

Figure 4:
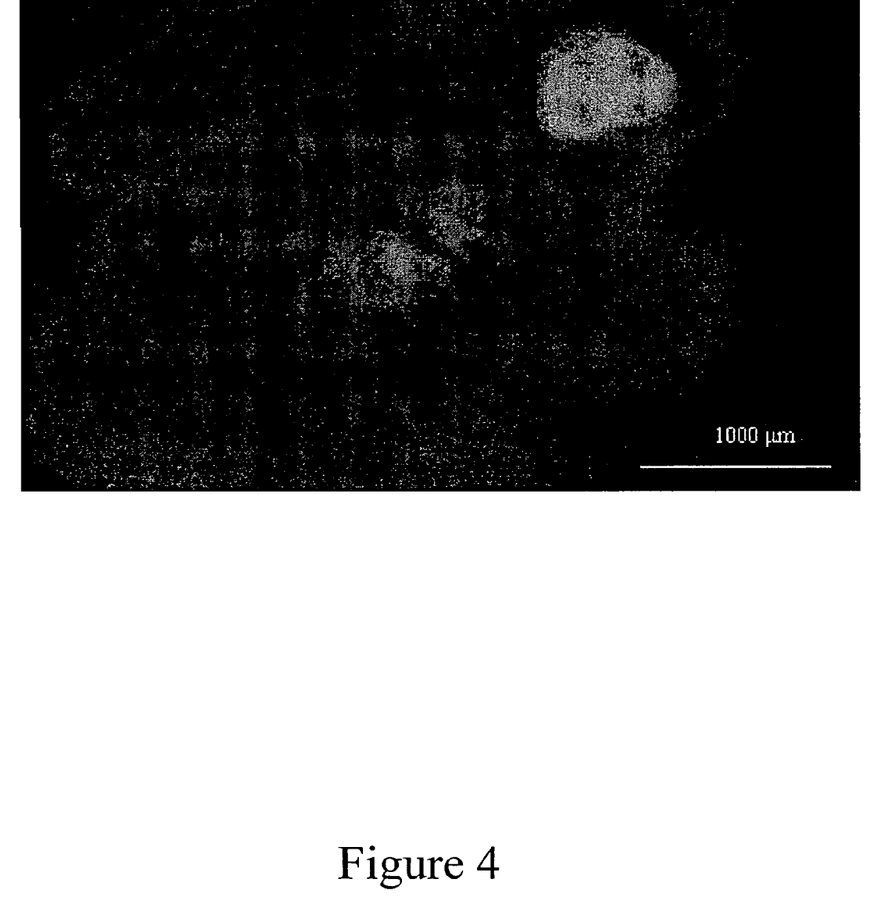
FIG. 4 shows a dual colored direct view of the Dunning-GFP and Dunning-RFP prostate tumor cells in the lobes of the mouse prostate through a lower abdominal wall skin flap window one day after SOI The bar is 1 mm.

In this instance, to visualize both GFP and RFP fluorescence at the same time, excitation was produced through a D425/60 band pass filter, 470DCXR dichroic mirror and emitted fluorescence was collected through a long pass filter GG475. Otherwise, the imaging was conducted as described in Example 1. Observations made showed both red and green fluorescence could be observed simultaneously. The opened skin flap allowed external direct view imaging of GFP tumor on the left-lateral lobe and RFP on the right-lateral lobe. These results are shown in FIG. 4.

EXAMPLE 6

Multicolor Imaging

Figure 5:
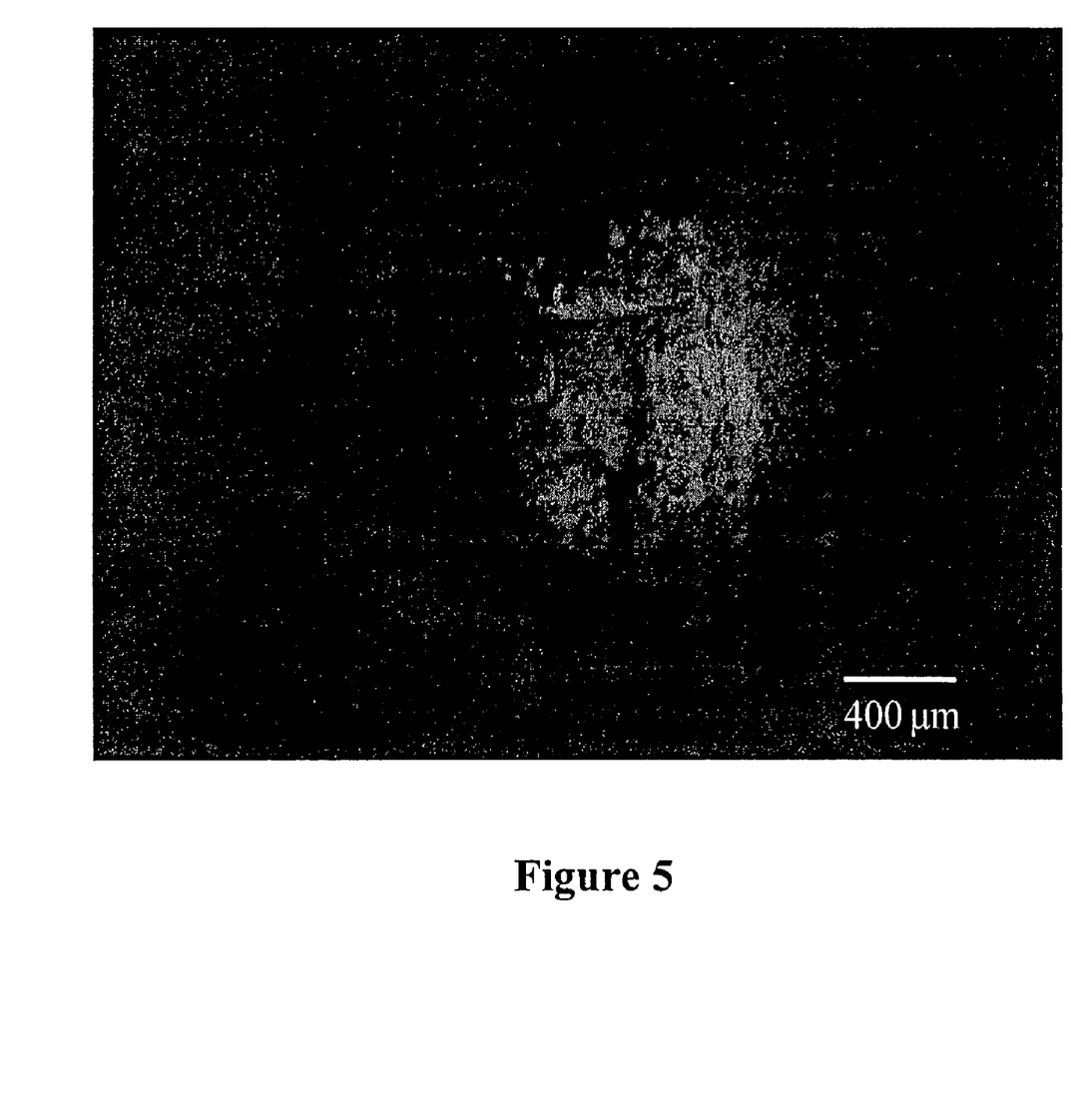
FIG. 5 shows GFP-HT-1080 and RFT-HT-1080 human fibrosarcoma cell growth from a mixture injected IV in a SCID mouse. The bar is 40 μm.

Samples of the human fibrosarcoma cell line, HT-1080 were modified to express GFP and RFT respectively as described in Preparations A and B above. A cell mixture of GFP-HT1080 and RFP-HT1080 was injected intravenously into a SCID mouse. The lung was imaged through the open skin flap in the chest wall of the living mouse 12 days after injection of the cell mixture. The results, in FIG. 5, show metastasis of both cell lines.

Figure 6:
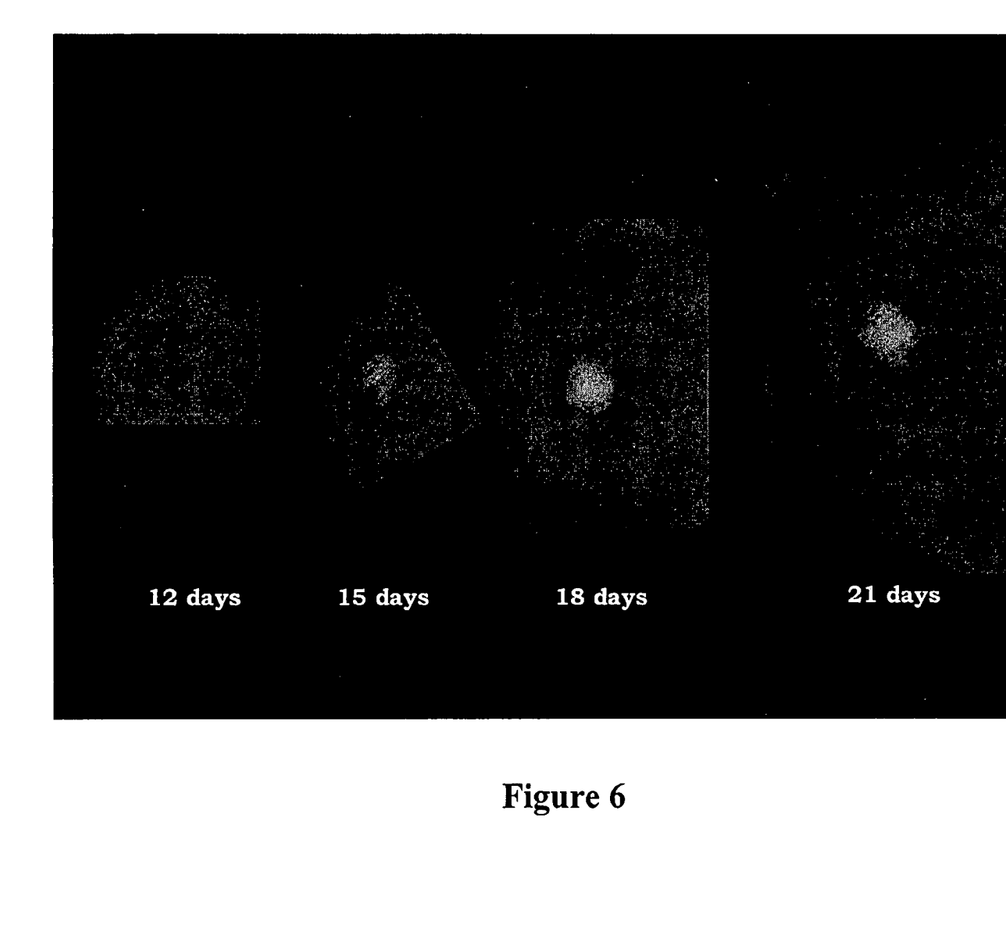
FIG. 6 shows the time course imaging of the lung metastasis shown in FIG. 5.
Figure 7A:
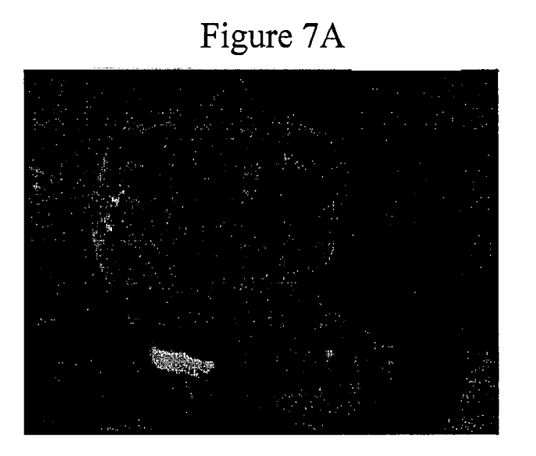
FIG. 7 shows a comparison of the growth of high and low metastastic breast cancer derived from MDA-MB-435-4A4-GFP and 2C5-RFP in nude mice.
Figure 7B:
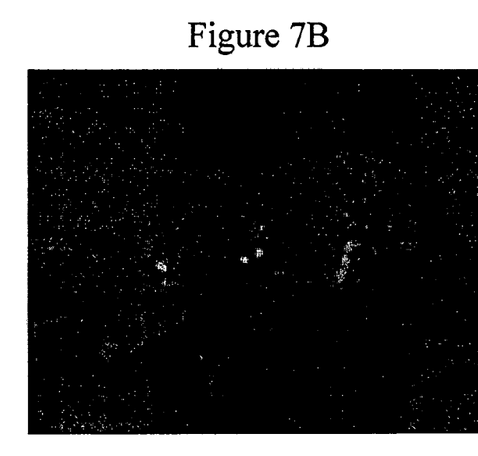
Figure 7C:
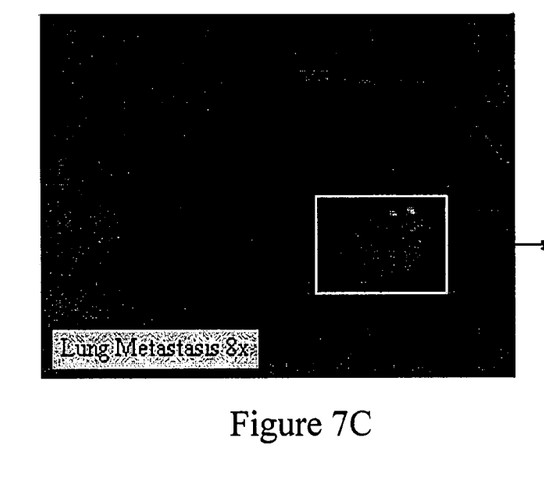
Figure 7D:
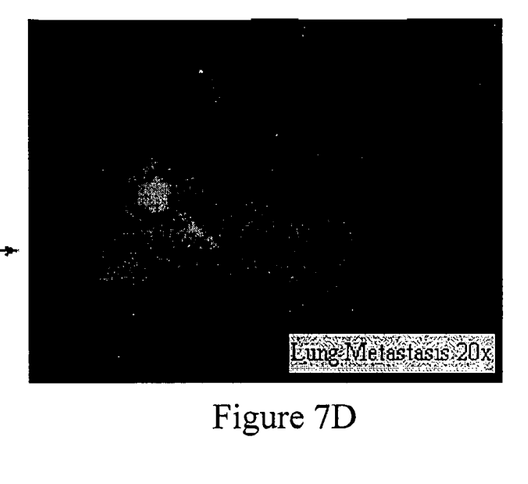

FIG. 6 shows similar results obtained in the same way as a function of time from 12 days after injection to 21-days after injection.

Figure 8:
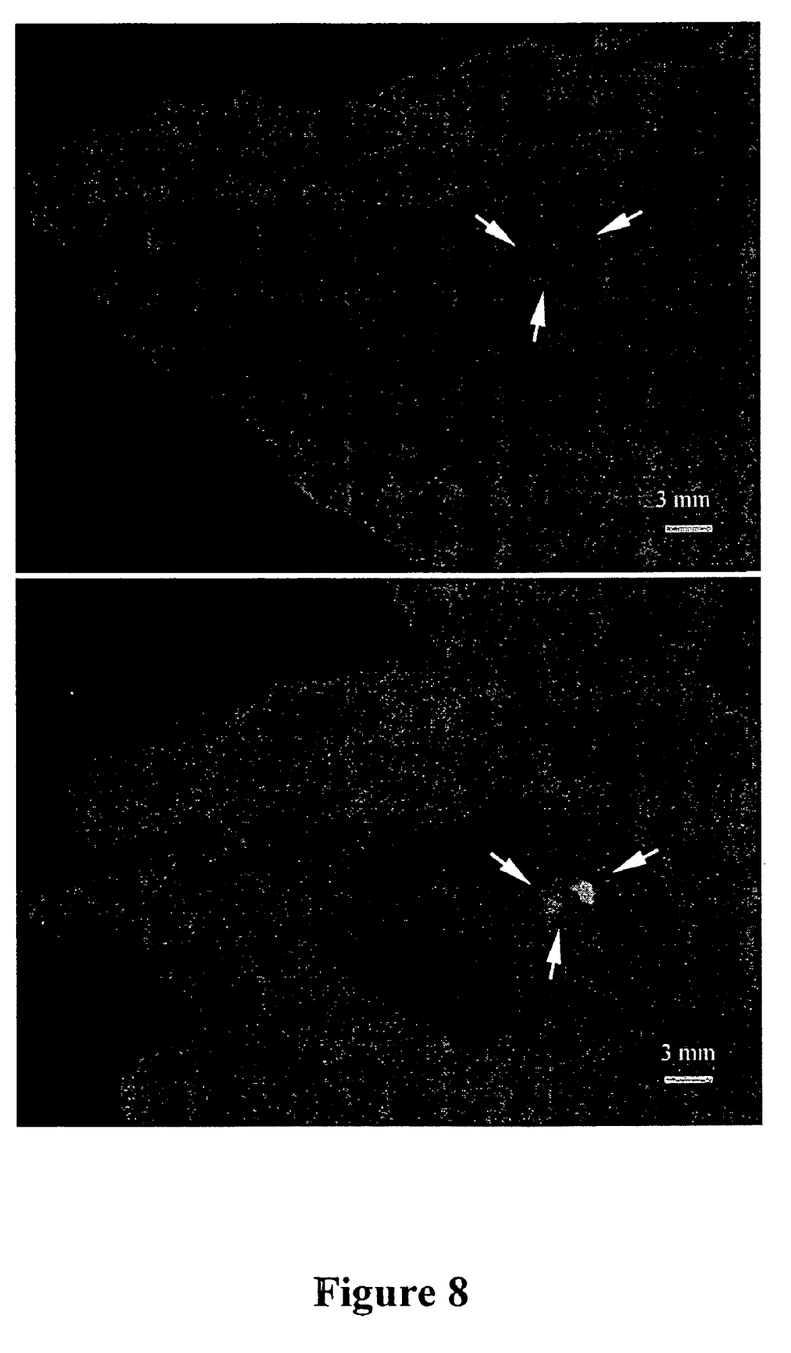
FIG. 8 shows a comparison of the tumor cells using whole body imaging rather than the skin flap method.

Similarly, immunocompromised mice were treated with both a rapidly metastasizing breast cancer cell line and a breast cancer cell line that metastasizes only slowly. The MDA-MB-435-4A4 cell line labeled with GFP and the 2C5 cell line labeled with RFP were injected into nude mice. The results using whole body imaging are shown in FIGS. 7 and 8. As shown, the two tumor types show different modes of growth.

Types of Tumors

The methods of the invention may be used to monitor the progression, angiogenesis or and/or metastasis of any type of cancer, including those exemplified as well as bone, kidney, bladder, ovary and the like. The invention method is applicable to any cancer model.

The invention claimed is:

1. A method to monitor progression, angiogenesis and/or metastasis of tumor cells or tissue on the internal organs in an animal having a tumor, which method comprises
   observing within the animal through an intact body wall or skull fluorescent tumor cells and/or tissue on the internal organs which are present at a suitable depth for observing in said animal through an opening of a skin flap and through a portion of the intact body wall or skull of the animal under the skin flap which remains when the skin and subcutaneous connective tissue of the skin flap is separated therefrom;
   wherein said animal is an immunocompromised or a syngeneic experimental animal, and
   wherein said skin flap is arranged to be reversibly opened and closed to permit observation of fluorescent tumor cells and/or tissue over time, whereby the progression, angiogenesis and/or metastasis of said tumor cells or tissue on the internal organs is monitored.

2. The method claim 1 wherein the immunocompromised experimental animal is a mouse or rat.

3. The method of claim 1 wherein said fluorescent tumor cells have been modified to contain a nucleic acid molecule for expression of a fluorescent protein.

4. The method of claim 3 wherein the fluorescent protein emits green fluorescence.

5. The method of claim 3 wherein the fluorescent protein emits red fluorescence.

6. The method of claim 1 wherein the experimental animal is provided tumor cells by subcutaneous injection.

7. The method of claim 1 wherein the experimental animal is provided tumor tissue by surgical orthological implantation (SOI).

8. The method of claim 1 wherein the tumor tissue is endogenous and is made fluorescent by infecting with a viral vector for expression of fluorescent proteins.

9. The method of claim 1 wherein the skin flap is an arc-shaped flap.

10. The method of claim 1 wherein the tumor cells or tissue are of brain, lung, liver, colon, breast, prostate, ovary or pancreas.

11. The method of claim 1 wherein the observing is macroscopic.

12. The method of claim 1 wherein the observing is microscopic.

13. The method of claim 1 wherein said tumor cells or tissue comprise nucleic acid molecules for production of fluorescent proteins of at least two different colors.

14. The method of claim 1 wherein the immunocompromised experimental animal is a nude or SCID rodent.

15. The method of claim 1 wherein the tumor cells or tissue are on the surface of the internal organs.

16. The method of claim 1 wherein the animal is a syngeneic experimental animal.

17. The method of claim 16 wherein the syngeneic experimental animal is a mouse or a rat.

* * * * *